United States Patent
Xu et al.

(10) Patent No.: US 10,018,555 B2
(45) Date of Patent: Jul. 10, 2018

(54) DEVICE AND METHOD FOR MEASURING CONCENTRATION OF ETCHANT

(71) Applicant: SHENZHEN CHINA STAR OPTOELECTRONICS TECHNOLOGY CO., LTD., Shenzhen, Guangdong (CN)

(72) Inventors: Rui Xu, Shenzhen (CN); Weiwei Zhang, Shenzhen (CN)

(73) Assignee: SHENZHEN CHINA STAR OPTOELECTRONICS TECHNOLOGY CO., LTD., Shenzhen (CN)

( * ) Notice: Subject to any disclaimer, the term of this patent is extended or adjusted under 35 U.S.C. 154(b) by 435 days.

(21) Appl. No.: 14/359,576

(22) PCT Filed: Mar. 28, 2014

(86) PCT No.: PCT/CN2014/074265
§ 371 (c)(1),
(2) Date: May 20, 2014

(87) PCT Pub. No.: WO2015/135230
PCT Pub. Date: Sep. 17, 2015

(65) Prior Publication Data
US 2015/0260651 A1    Sep. 17, 2015

(30) Foreign Application Priority Data
Mar. 12, 2014 (CN) .......................... 2014 1 0091097

(51) Int. Cl.
*G01N 21/31* (2006.01)
(52) U.S. Cl.
CPC .................................. *G01N 21/31* (2013.01)

(58) Field of Classification Search
CPC .......... C23F 1/08; G01N 21/31; G01N 21/59; G01N 21/01; B01D 53/40; G01J 3/42
(Continued)

(56) References Cited

U.S. PATENT DOCUMENTS 3,147,095 A * 9/1964 Kanuch .................. B01D 53/26
  96/113
5,747,809 A * 5/1998 Eckstrom ........... G01N 21/3504
  250/339.13

(Continued)

OTHER PUBLICATIONS

Non-Patent Literature "Material Safety Data Sheet", published Apr. 2004*

(Continued)

*Primary Examiner* — Manish S Shah
*Assistant Examiner* — Irving A Campbell

(57) ABSTRACT

A device and method for measuring concentration of etchant, the device comprises a concentration measuring mechanism and an acid mist elimination mechanism connected with the concentration measuring mechanism, the acid mist elimination mechanism is configured to eliminate acid mist inside the concentration measuring mechanism, and the concentration measuring mechanism is configured to receive etchant in real time, measure absorbance of each kind of acid of the etchant in a non-acid mist environment, and calculate concentration of each kind of acid of the etchant according to the absorbance. It can overcome the interference of the acid mist on concentration measurement of the acid of the acid mixture etchant. In this way, the concentration of each kind of acid of the acid mixture etchant can be online measured rapidly and accurately, and the desiccative gas can be recycled, which achieves the effect of resource conservation.

6 Claims, 1 Drawing Sheet

(58) Field of Classification Search
USPC .................... 73/61.48; 137/15.04; 359/509; 356/432–444
See application file for complete search history.

(56) References Cited

U.S. PATENT DOCUMENTS

| | | | | |
|---|---|---|---|---|
| 5,895,918 | A * | 4/1999 | Powell | G01J 3/453 |
| | | | | 250/339.08 |
| 6,369,387 | B1 * | 4/2002 | Eckles | G01N 21/3504 |
| | | | | 250/343 |
| 7,016,039 | B2 * | 3/2006 | Breninger | G01J 1/02 |
| | | | | 356/364 |
| 2005/0202564 | A1 * | 9/2005 | Lee | G01N 21/359 |
| | | | | 436/55 |
| 2008/0110743 | A1 * | 5/2008 | Whitlock | B01D 53/40 |
| | | | | 203/4 |

OTHER PUBLICATIONS

Non-Patent Literature "Spectrometric analysis of process etching solutions of the photovoltaic industry-Determination of HNO3, HF, and H2SiF6 using high-resolution continuum source absorption spectrometry of diatomic molecules and atoms", published Apr. 2, 2012*

* cited by examiner

DEVICE AND METHOD FOR MEASURING CONCENTRATION OF ETCHANT

FIELD OF THE INVENTION

The present invention relates to the field of etchant, and more particularly, relates to a device and a method for measuring concentration of etchant.

BACKGROUND

Wet etching is the core technique for patterning metal film using acid etchant and forming Gates, Source-Drains, and Indium Tin Oxides (ITO) electrodes in thin-film transistor (TFT hereinafter) manufacturing process. Wherein, Aluminum and Molybdenum are often configured as conducting material to form the Gates, the etchant can be different kinds of acid, but the metal film is mostly dissolved, oxidized, and reduced by strong acid mixture (e.g., mixed phosphoric acid, phosphoric acid, and acetic acid), so that the Gate film is patterned. The acid mixture serving as the etchant is generally composed of phosphoric acid (70%-72%), nitric acid (1.8%-2.0%), and acetic acid (9.5%-10.5%). Wherein, the nitric acid is configured to supply $H_3O^+$ and oxidize the metal (e.g., Aluminum and Molybdenum) for etching, the phosphoric acid provides phosphate radical, and can form complex with the oxidized metal to dissolve the metal oxides, the acetic acid can stick to the surface of the reactants, and thereby reduce the viscosity of the etchant, increase invasion of the etchant, and adjust the etching rate. In the etching process for forming the Gates and the Source-Drains, the concentration of the acid mixture is to reduce gradually due to the constant consumption of the nitric acid and the acetic acid, and then the etching quality may be adversely affected. In order to avoid bad etching effect and maintain the etching rate and the etching quality, accurately controlling the concentration of the nitric acid and the acetic acid is very important. Therefore, additional nitric acid and acetic acid should be continually added into the acid mixture etchant for maintaining the compositional ratio of the acid mixture etchant in the etching process. Accordingly, the manufacturing process needs an online monitoring device configured to control the concentration of each kind of acid of the acid mixture etchant and thereby ensure an appropriate etching rate and good etching quality.

As shown in FIG. 1, a conventional online monitoring device generally uses an online optical concentration measuring mechanism based on Lambert-Beer theory to monitor the concentration of each kind of acid of the acid mixture etchant in the etching process. The measurement principle is as follow: a light source 210 emits light with multiple wavelengths; the light passes through a monochromator 220 to generate light with specific wavelengths; the light with the specific wavelengths passes through a reference cell 240 and a sample cell 230 containing the acid mixture, which are arranged in parallel; a detector 250 measures the difference between absorbance of the sample cell 230 and absorbance of the reference cell 240; and finally the concentration of each kind of acid of the acid mixture in the sample cell 230 is calculated using Lambert-Beer theory.

However, in an actual production, an optical concentration measuring mechanism is a sealed container. Compared with external pipes, the online optical concentration measuring mechanism is always in the state of negative pressure. The acid mixture transported into the sample cell 230 through acid transporting pipe (not labeled in figures) will inevitably slightly volatilize at the joint of the acid transporting pipe and the sample cell 230, especially low boiling acetic acid will volatilize seriously. Lingering acid mist will be formed in the sealed negative pressure system of the online optical concentration measuring mechanism over time, and the surface of the sample cell 230 or the surface of the reference cell 240 may be covered by the acid mist. Thus, light adsorption may be adversely affected, and measured value of the acid concentration may be adversely affected too. The measured value of the acid concentration may be lower or higher than the real value, which may result in that the acid supplement system complements excessive or insufficient acid, and the concentration of the acid in the etchant is too large or too small. Thus, a large quantity of etching defects may occur, which may need much rework and/or repair, and cause great losses in the production. In practical use, to overcome the acid mist phenomenon, it is necessary to dismantle the online optical concentration measuring mechanism or wipe the measuring cell periodically. These operations may destroy precision of the measuring mechanism, and the reassembled online optical concentration measuring mechanism needs to be recalibrated before being configured again, which brings a lot of inconvenience to the actual production.

SUMMARY

The objective of the present invention is to provide a device and a method for measuring concentration of etchant, which can rapidly, economically, and accurately measure the concentration of each kind of acid in the etchant in the etching process, aiming at the drawback in the prior art that the acid mist is formed inside the online optical concentration measuring mechanism and may interfere with the measurement of the concentration of the acid in the acid mixture.

The technical solutions of the present invention for solving the technical problems are as follows:

A device for measuring concentration of etchant, the device comprises a concentration measuring mechanism and an acid mist elimination mechanism connected with the concentration measuring mechanism, the acid mist elimination mechanism is configured to eliminate acid mist inside the concentration measuring mechanism, and the concentration measuring mechanism is configured to receive etchant in real time, measure absorbance of each kind of acid of the etchant in a non-acid mist environment, and calculate concentration of each kind of acid of the etchant according to the absorbance.

Advantageously, the device further comprises a filling tank configured for containing the etchant and connected with the concentration measuring mechanism, the filling tank is further configured to supply the etchant to the concentration measuring mechanism in real time.

Advantageously, the acid mist elimination mechanism contains desiccative gas, a circulation circuit is formed between the acid mist elimination mechanism and concentration measuring mechanism, and the desiccative gas inside the acid mist elimination mechanism is configured to extract the acid mist from the concentration measuring mechanism, and then the extracted acid mist is dried, and finally the desiccative gas is recycled into the concentration measuring mechanism.

Advantageously, the acid mist elimination mechanism includes:

an inlet pipe and an outlet pipe respectively connected with the concentration measuring mechanism;

a gas tank fixedly connected with the inlet pipe, the desiccative gas contained in the gas tank; and a drying tank disposed between the outlet pipe and the gas tank;

the gas tank, the inlet pipe, the concentration measuring mechanism, the outlet pipe, and the drying tank form the circulation circuit, and the drying tank contains drying agent.

Advantageously, the desiccative gas inside the gas tank is air or nitrogen gas.

Advantageously, the drying agent is a mixture of calcium oxide and sodium hydroxide.

Advantageously, further comprising a one-way pipe configured to communicate the drying tank with the gas tank, the desiccative gas dried by the drying tank will return to the gas tank through the one-way pipe.

Advantageously, the etchant by weight percentage includes 70%-72% phosphoric acid, 1.8-2.0% nitric acid, 9.5-10.5 acetic acid, and marginal water.

Advantageously, the inlet pipe is provided with a first valve for regulating flow rate of the desiccative gas in the gas tank, and the one-way pipe is provided with a second valve for regulating flow rate of the desiccative gas in the drying tank.

A device for measuring concentration of etchant, the device comprises a concentration measuring mechanism, a filling tank configured to supply the etchant to the concentration measuring mechanism in real time and an acid mist elimination mechanism connected with the concentration measuring mechanism, the acid mist elimination mechanism includes:

an inlet pipe and an outlet pipe respectively connected with the concentration measuring mechanism;

a gas tank fixedly connected with the inlet pipe, the gas tank contains desiccative gas;

a drying tank disposed between the outlet pipe and the gas tank, the gas tank, the inlet pipe, the concentration measuring mechanism, the outlet pipe, and the drying tank form a circulation circuit, the drying tank contains drying agent;

the desiccative gas flow into the concentration measuring mechanism through the inlet pipe and is configured to the acid mist from the concentration measuring mechanism, and then the extracted acid mist is dried through the drying tank, finally the dried desiccative gas is recycled into the concentration measuring mechanism;

the concentration measuring mechanism is configured to receive the etchant in real time and measure absorbance of each kind of acid of the etchant in a non-acid mist environment, and calculate concentration of each kind of acid of the etchant according to the absorbance.

Advantageously, the desiccative gas in the gas tank is air or nitrogen gas.

Advantageously, the drying agent is a mixture of calcium oxide and sodium hydroxide.

Advantageously, further comprising a one-way pipe configured to communicate the drying tank with the gas tank, the desiccative gas dried by the drying tank will return to the gas tank through the one-way pipe.

Advantageously, the etchant by weight percentage includes 70%-72% phosphoric acid, 1.8-2.0% nitric acid, 9.5-10.5 acetic acid, and marginal water.

Advantageously, the inlet pipe is provided with a first valve for regulating flow rate of the desiccative gas in the gas tank, and the one-way pipe is provided with a second valve for regulating flow rate of the desiccative gas in the drying tank.

A method for measuring concentration of etchant, using a device for measuring concentration of etchant, the device for measuring concentration of etchant comprises a concentration measuring mechanism, a filling tank for supplying etchant to the concentration measuring mechanism, and an acid mist elimination mechanism configured to eliminate acid mist inside the concentration measuring mechanism; the method comprising the following steps:

connecting the acid mist elimination mechanism with the concentration measuring mechanism;

connecting the filling tank with the concentration measuring mechanism;

flowing the etchant in the filling tank into the concentration measuring mechanism, and turning on the acid mist elimination mechanism to extract acid mist from the concentration measuring mechanism, dry the extracted acid mist, and recycle desiccative gas into the concentration measuring mechanism for continuing to extract acid mist;

using the concentration measuring mechanism to measure absorbance of each kind of acid of the etchant in a non-acid mist environment in real time, and calculate concentration of each kind of acid of the etchant according to the absorbance.

By implementing the device and the method for measuring concentration of etchant of the present invention, the following advantages can be achieved: the acid mist elimination mechanism connected with the concentration measuring mechanism is provided, and a circulation circuit is formed between the acid mist elimination mechanism and concentration measuring mechanism. The acid mist elimination mechanism is configured to eliminate the acid mist formed by etchant evaporation in the concentration measuring mechanism, and can overcome the interference of the acid mist on concentration measurement of the acid of the acid mixture etchant. In this way, the concentration of each kind of acid of the acid mixture etchant can be online measured rapidly and accurately, and the desiccative gas can be recycled, which achieves the effect of resource conservation.

BRIEF DESCRIPTION OF THE DRAWINGS

The present invention will be further described with reference to the accompanying drawings and embodiments in the following, in the accompanying drawings.

DETAILED DESCRIPTION

To make the technical feature, objective and effect of the present invention be understood more clearly, now the specific implementation of the present invention is described in detail with reference to the accompanying drawings and embodiments.

Figure 1:
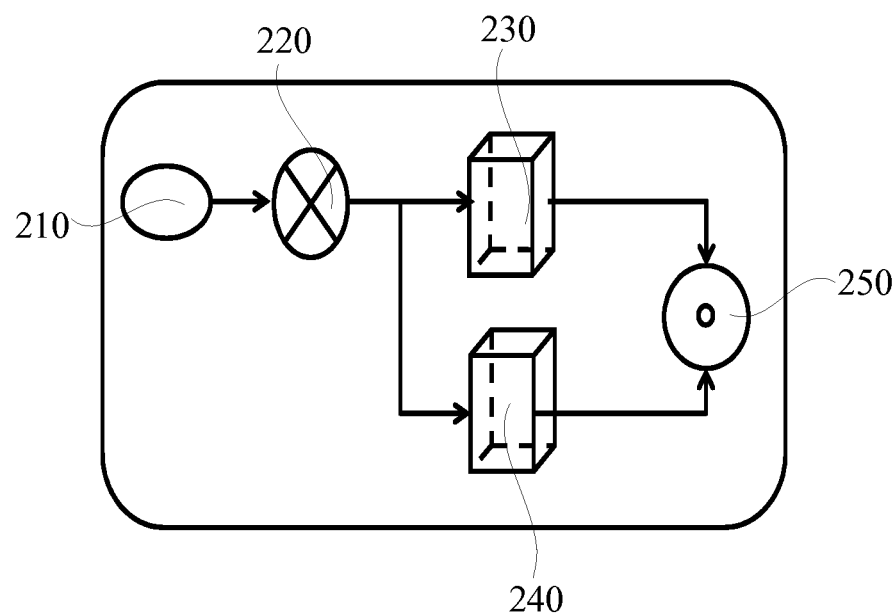
FIG. 1 is an internal structural block diagram of a concentration measuring mechanism in the prior art.
Figure 2:
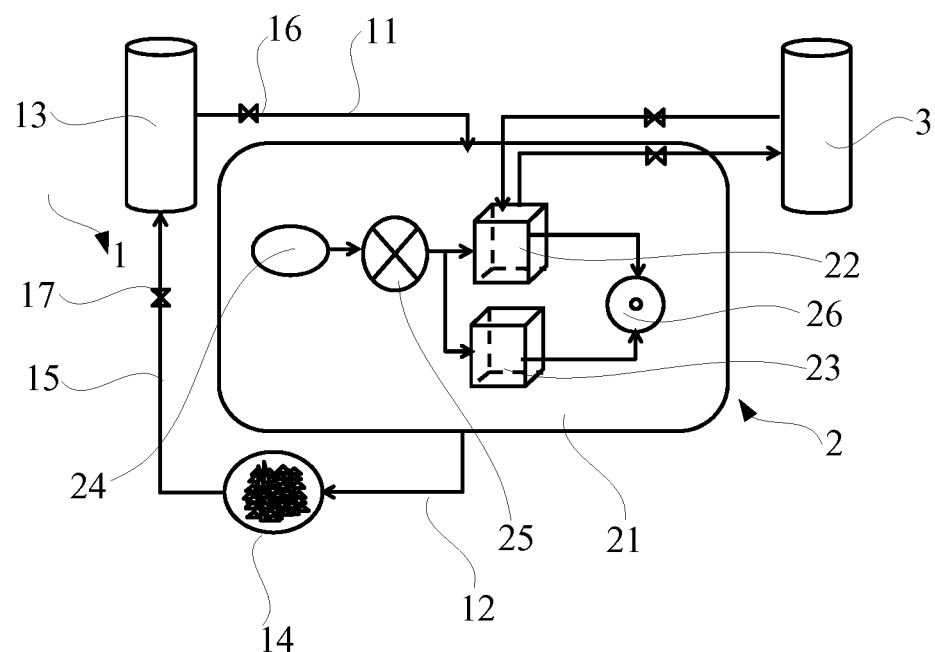
FIG. 2 is a structural block diagram of a device for measuring concentration of etchant of a preferred embodiment of the present invention.

As shown in FIG. 1, a preferred embodiment of the present invention provides a device for measuring concentration of etchant, which comprises an acid mist elimination mechanism 1, a concentration measuring mechanism 2, and a filling tank 3. Wherein, the filling tank 3 contains etchant, and is configured to online supply the etchant to the concentration measuring mechanism 2 in real time; the acid mist elimination mechanism 1 is connected with the concentration measuring mechanism 2, and configured to eliminate the acid mist inside the concentration measuring mechanism 2, so that the concentration measuring mechanism 2 can measure absorbance of acid mixture of the etchant in a non-acid mist environment in real time, and calculate concentration of each kind of acid mixture of the etchant. In this way, concentration measurement can be more accurate, the concentration of each kind of acid of the etchant can be controlled and monitored accurately, and quality of etching can be improved.

Furthermore, the acid mist elimination mechanism 1 contains desiccative gas, and a circulation circuit is formed between the acid mist elimination mechanism 1 and concentration measuring mechanism 2. The desiccative gas inside the acid mist elimination mechanism 1 is configured to extract acid mist from the concentration measuring mechanism 2. The extracted acid mist is dried, and the dried desiccative gas is recycled into the concentration measuring mechanism 2 and continues to extract acid mist. The process is repeated so that the circulation circuit is formed between the acid mist elimination mechanism 1 and concentration measuring mechanism 2, and thus the rational utilization of resources is realized.

The filling tank 3 is configured to contain the etchant, and the filling tank 3 is connected to an etching machine (not shown) through a pipeline to supply required etchant for TFT manufacturing processes. In the embodiment, the filling tank 3 and the concentration measuring mechanism 2 are bidirectionally online connection, so that the etchant in the filling tank 3 can flow into the concentration measuring mechanism 2 to enable the measurement of the concentration of each kind of acid of the etchant, and the measured etchant can flow back into the filling tank 3 through the pipeline to achieve the recycling use of the etchant. Preferably, the etchant of the filling tank 3 is Aluminium etchant, and the etching by weight percentage includes 70%-72% phosphoric acid, 1.8-2.0% nitric acid, 9.5-10.5 acetic acid, and marginal water.

The concentration measuring mechanism 2 measures the concentration of each kind of acid of the etchant based on Lambert-Beer theory, and the concentration measuring mechanism 2 is connected with the filling tank 3 online to achieve online measurement of the concentration and absorbance of each kind of acid of the mixture acid etchant in the filling tank 3 in real time.

The concentration measuring mechanism 2 is an airtight container, and includes a sealed cavity 21, a light source 24 received in the sealed cavity 21, a monochromator 25, a sample cell 22, a reference cell 23, and a detector 26. Compared with other external pipelines out of the concentration measuring mechanism 2, the sealed cavity 21 is always in a state of negative pressure, so that the etchant of the external filling tank 3 can flow into the sealed cavity 21. The sample cell 22 and the reference cell 23 have the same optical path and are arranged to be parallel to each other, and the monochromator 25 and the detector 26 are respectively arranged on two opposite sides of each of the sample cell 22 and the reference cell 23. The measuring principle of the concentration measuring mechanism 2 is as follow: light emitted from the light source 24 passes through the monochromator 25, and passes the parallel arranged sample cell 22 and reference cell 23 respectively; the detector 26 measures the difference between absorbance of the sample cell 22 and absorbance of the reference cell 23, and the difference between concentration of the sample cell 22 and concentration of the reference cell 23 is calculated according to the absorbance difference. The working principle of the concentration measuring mechanism 2 is the prior art, and therefore does not need to be repeated here. In this embodiment, the sample cell 22 and the filling tank 3 are bidirectionally connected together, so that the etchant in the filling tank 3 can flow into the sample cell 22 to enable online and real time measurement of the concentration of each kind of acid of the acid mixture etchant, and the measured etchant can flow back into the filling tank 3 through the pipeline to achieve the recycling use of the etchant.

The reference cell 23 contains water solution, and the sample cell 22 contains the etchant, therefore, the concentration difference measured by the concentration measuring mechanism 2 is actually the concentration of each kind of the acid of the etchant in the sample cell 22. That is, the concentration measuring mechanism 2 measures the concentrations of nitric acid, phosphoric acid, and acetic acid of the etchant in the etching process. In the etching process, by comparing the measured concentrations of nitric acid, phosphoric acid, and acetic acid with desired standard concentration of each kind of the acid of the etchant, desired addition amount of nitric acid, phosphoric acid, and acetic acid can be obtained. Thus, nitric acid, acetic acid, and for phosphoric acid can be added into the filling tank 3 in time to ensure etching rate and etching quality in the etching process. In other embodiments, the reference cell 23 can be empty, that is, nothing is contained in the reference cell 23.

Meanwhile, when the etchant in the filling tank 3 is supplied to the sample cell 22, the acid of the etchant will inevitably volatile through the interface between the outside acid pipe and the sample cell 22, especially low boiling acetic acid of the etchant will volatile seriously. More and more acid mist will fill the concentration measuring mechanism 2 over time, and the acid mist will spread in the concentration measurement mechanism 2 and stay in the sealed cavity 21. With time elapsing, more and more acid mist will be filled in the sealed cavity 21.

A circulation circuit is formed between the acid mist elimination mechanism 1 and concentration measuring mechanism 2, and the acid mist elimination mechanism 1 is configured to eliminate the acid mist in the concentration measuring mechanism 2. The acid mist elimination mechanism 1 includes an inlet pipe 11, an outlet pipe 12, a gas tank 13, a drying tank 14, and a one-way pipe 15.

The inlet pipe 11 and the outlet pipe 12 are disposed outside the concentration measurement mechanism 2, and both the inlet pipe 11 and the outlet pipe 12 are connected with the concentration measurement mechanism 2. The gas tank 13 contains desiccative gas, and the gas tank 13 is connected with the inlet pipe 11. One end of the drying tank 14 is connected with the outlet pipeline 12, and the other end of the drying tank 14 is connected with the gas tank 13 through the one-way pipe 15, that is, the drying tank 14 is disposed between the outlet pipe 12 and the gas tank 13. Therefore, the gas tank 13, the inlet pipe 11, the concentration measuring mechanism 2, the outlet pipe 12, the drying tank 14, and the one-way pipe 15 are connected one by one to form a closed circulation circuit. The drying tank 14 contains drying agent to absorb the acid mist and water vapor, specifically, the drying agent is a mixture of calcium oxide and sodium hydroxide.

Wherein, the desiccative gas in the gas tank 13 is air or nitrogen gas, and preferably the desiccative gas is inert nitrogen. When the desiccative gas in the gas tank 13 flows into the sealed cavity 21 through the inlet pipe 11, internal pressure of the sealed cavity 21 continuously increases with continuous inflow of the desiccative gas. When the internal pressure of the sealed cavity 21 is equal to or more than the external pressure, the desiccative gas in the sealed cavity 21 will carry the acid mist in the sealed cavity 21 into the drying tank 14 through the outlet pipe 12. Because the drying tank 14 contains the drying agent, the acidic material and water vapor flowing from the sealed cavity 21 are adsorbed and dried by the drying agent in the drying tank 14, so that the gas flowing from the drying tank 14 contains only the desiccative gas (i.e., not containing the acid mist and water vapor). Furthermore, the desiccative gas flows back into the gas tank 13 through the one-way pipe 15, and then flows into the concentration measuring mechanism 2 to carry acid mist again. Thus, the desiccative gas is recycled, and resource conservation is realized. Specifically, when the desiccative gas carries the acid mist in the sealed cavity 21 into the drying tank 14 through the outlet pipe 12, calcium oxide in the drying tank 14 absorbs the water vapor of the gas mixture, and sodium hydrate adsorbs the acidic material, so that the gas flowing from the drying tank 14 contains only the desiccative gas, and thus rational use of resource is achieved. When the quantity of the water vapor and the acidic material adsorbed by the drying agent in the drying tank 14 exceeds a predetermined level, the drying agent will fail, and the drying agent in the drying tank 14 can be replaced.

In this embodiment, the inlet pipe 11 and the outlet pipe 12 can be connected with the concentration measurement mechanism 2 by welding, riveting, threaded connections, or other conventional connection methods, and the connection method is no limit here. In order to control the flow rate of the desiccative gas in the gas tank 13, the inlet pipe 11 is provided with a first valve 16, and the first valve 16 is configured to regulate the flow rate of the desiccative gas in the gas tank 13. When there is much acid mist in the concentration measurement mechanism 2, correspondingly, the flow rate of the desiccative gas can be increased by operating the first valve 16. Similarly, the one-way pipe 15 is provided with a second valve 17 for regulating the flow rate of the desiccative gas, and the flow rate of the desiccative gas flowing from the drying tank 14 into the gas tank 13 is regulated by operating the second valve 17.

In the device for measuring concentration of etchant of the present invention, the acid mist elimination mechanism 1 connected with the concentration measuring mechanism 2 is provided. A circulation circuit is formed between the acid mist elimination mechanism 1 and concentration measuring mechanism 2, and the acid mist elimination mechanism 1 is configured to eliminate the acid mist formed by etchant evaporation in the concentration measuring mechanism 2. Thus, the interference of the acid mist on concentration measurement of the acid of the acid mixture etchant is overcome, and the goal of accurately controlling and monitoring the concentration of each kind of acid of the etchant is achieved. Specifically, the gas tank 13, the inlet pipe 11, the concentration measuring mechanism 2, the outlet pipe 12, and the drying tank 14 form the circulation circuit, the desiccative gas in the gas tank 13 can flow into the concentration measuring mechanism 2 through the inlet pipe 11, extract the acid mist from the concentration measuring mechanism 2, and further flow from the outlet pipe 12 into the drying tank 14. When the acid mist is absorbed and dried by the drying agent in the drying tank 14, the desiccative gas is recycled into the gas tank 13 through the one-way pipe 15. The device of the present invention overcomes the interference of the acid mist on concentration measurement of the acid of the acid mixture etchant, and the concentration of each kind of acid of the acid mixture etchant can be online measured rapidly and accurately. The desiccative gas can be recycled, which achieves the effect of resource conservation. The concentration measuring mechanism 2 does not need to be dismantled and cleaned, and thus the service life of the concentration measuring mechanism 2 is increased.

In another aspect of the present invention, a method for measuring concentration of etchant is provided. The method can be implemented by the above-mentioned device for measuring concentration of etchant. The device for measuring concentration of the etchant comprises a concentration measuring mechanism 2, a filling tank 3 configured to supply etchant to the concentration measuring mechanism 2, and an acid mist elimination mechanism 1 configured to eliminate acid mist in the concentration measuring mechanism 2; and a circulation circuit is formed between the acid mist elimination mechanism 1 and concentration measuring mechanism 2. Specifically, the connection relations of the acid mist elimination mechanism 1, the concentration measuring mechanism 2, and the filling tank 3 have been detailed in the above embodiment of the device for measuring concentration of etchant, and therefore do not need to be repeated here.

The method for measuring concentration of etchant comprises the following steps:
connecting the acid mist elimination mechanism 1 with the concentration measuring mechanism 2;
online connecting the filling tank 3 with the concentration measuring mechanism 2;
flowing the etchant from the filling tank 3 into the concentration measuring mechanism 2, and turning on the acid mist elimination mechanism 1 to extract acid mist from the concentration measuring mechanism 2 by desiccative gas, dry the extracted acid mist, and recycle the desiccative gas into the concentration measuring mechanism 2 for continuing to extract acid mist;
using the concentration measuring mechanism 2 to measure absorbance of each kind of acid of the etchant in a non-acid mist environment in real time, and calculate concentration of each kind of acid of the etchant according to the absorbance.

In the method for measuring concentration of etchant of the present invention, at first, the first the gas tank 13, the inlet pipe 11, the concentration measuring mechanism 2, the outlet pipe 12, the drying tank 14, and the one-way pipe 15 are connected one by one to form a circulation circuit. The reference cell 23 is filled with water as the reference solution, and the filling tank 3 is filled with the etchant and is bidirectionally connected with the concentration measuring mechanism 2. Specifically, the filling tank 3 and the sample cell 22 form a bidirectional online connection to flow the etchant of the filling tank 3 into the sample cell 22 online. The first valve 16 of the inlet pipe 11 and the second valve 17 of the one-way pipe 15 are then opened, the desiccative gas in the gas tank 13 flows into the concentration measuring mechanism 2 and extracts acid mist from the concentration measuring mechanism 2, and the desiccative gas is recycled. Finally, the concentration measuring mechanism 2 measures the difference between absorbance of the etchant of the sample cell 22 and absorbance of water solution of the reference cell 23, and the absorbance difference is actually the absorbance of each kind of acid of the etchant in the sample cell 22. Thus, the concentration of each kind of acid of the etchant can be calculated according to the absorbance. The specific way to calculate the concentration according to the absorbance is the prior art, and therefore does not need to be repeated here. The acid mixture of the etchant of the sample cell 22 flows back into the filling tank 3 through pipelines after the concentration measurement of each kind of acid of the etchant is completed, so that the recycling use of the etchant is achieved.

In the method for measuring concentration of etchant of the present invention, the acid mist can be extracted from the concentration measuring mechanism 2 timely, and the interference of the acid mist on concentration measurement of each kind of acid of the etchant is overcome, so that the concentration of each kind of acid of the etchant is controlled and monitored accurately. Furthermore, the concentration of each kind of acid of the etchant can be online measured in real time, so that nitric acid, acetic acid, and/or phosphoric acid can be added in time to ensure accurate ratio of each kind of acid of the etchant in the etching process, and high-precision etching images can be obtained.

The present application has been described with the drawings to the embodiments, while the present application is not limit to the aforementioned specific embodiments and the specific embodiments are merely a hint rather than a limit. It will be understood by those skilled in the art that various changes may be made and equivalents may be substituted without departing from the purpose of the application and the scope of the claims, but all the changes will be included within the scope of the appended claims.

The invention claimed is:

1. A device for measuring concentration of etchant, wherein; the device comprises a concentration measuring mechanism and an acid mist elimination mechanism connected with the concentration measuring mechanism, the acid mist elimination mechanism is configured to eliminate acid mist inside the concentration measuring mechanism, and the concentration measuring mechanism is configured to receive etchant in real time, measure absorbance of each kind of acid of the etchant in a non-acid mist environment, and calculate concentration of each kind of acid of the etchant according to the absorbance; wherein, when the concentration is calculated, the concentration measuring mechanism is in a negative pressure state;

wherein the acid mist elimination mechanism contains desiccative gas, a circulation circuit is formed between the acid mist elimination mechanism and concentration measuring mechanism, the desiccative gas inside the acid mist elimination mechanism is configured to extract the acid mist from the concentration measuring mechanism, and then the extracted acid mist is dried, and finally the desiccative gas is recycled into the concentration measuring mechanism;

wherein the acid mist elimination mechanism comprises: a gas tank, an inlet pipe and an outlet pipe respectively connected with the concentration measuring mechanism; the gas tank fixedly connected with the inlet pipe, the desiccative gas contained in the gas tank; and a drying tank disposed between the outlet pipe and the gas tank; the gas tank, the inlet pipe, the concentration measuring mechanism, the outlet pipe, and the drying tank form a circulation circuit, and the drying tank contains a drying agent; the inlet pipe is provided with a first valve for regulating flow rate of the desiccative gas in the gas tank, and the one-way pipe is provided with a second valve for regulating flow rate of the desiccative gas in the drying tank, and a one-way pipe configured to communicate the drying tank with the gas tank;

wherein the desiccative gas dried by the drying tank returns to the gas tank through the one-way pipe; and the device further comprises a filling tank configured for containing the etchant and connected with the concentration measuring mechanism, the filling tank further configured to supply the etchant to the concentration measuring mechanism in real time;

the acid mist elimination mechanism is configured to eliminate acid mist inside the concentration measuring mechanism by using the desiccative gas in the gas tank to adjust a gas pressure in the concentration measuring mechanism and to bring the acid mist out of the concentration measuring mechanism;

the concentration measuring mechanism comprises a sample cell and a reference cell, the sample cell and the filling tank are bidirectionally connected together, so that the etchant in the filling tank can flow into the sample cell to enable online and real time measurement of the concentration of each kind of acid of the acid mixed etchant, and the measured etchant can flow back into the filling tank through the pipeline to achieve the recycling use of the etchant.

2. The device for measuring concentration of etchant according to claim 1, wherein the desiccative gas inside the gas tank is air or nitrogen gas.

3. The device for measuring concentration of etchant according to claim 1, wherein the drying agent is a mixture of calcium oxide and sodium hydroxide.

4. The device for measuring concentration of etchant according to claim 1, wherein the etchant by weight percentage includes 70%-72% phosphoric acid, 1.8-2.0% nitric acid, 9.5-10.5 acetic acid, and marginal water.

5. A device for measuring concentration of etchant, wherein the device comprises a concentration measuring mechanism, a filling tank configured to supply the etchant to the concentration measuring mechanism in real time and an acid mist elimination mechanism connected with the concentration measuring mechanism, the acid mist elimination mechanism including:

an inlet pipe and an outlet pipe respectively connected with the concentration measuring mechanism;

a gas tank fixedly connected with the inlet pipe, the gas tank containing desiccative gas;

a drying tank disposed between the outlet pipe and the gas tank, the gas tank, the inlet pipe, the concentration measuring mechanism, the outlet pipe, and the drying tank forming a circulation circuit, the drying tank containing a drying agent;

the desiccative gas flow into the concentration measuring mechanism through the inlet pipe and is configured to eliminate the acid mist from the concentration measuring mechanism, and then the extracted acid mist is dried through the drying tank, finally the dried desiccative gas is recycled into the concentration measuring mechanism;

the concentration measuring mechanism being configured to receive the etchant in real time and measure absorbance of each kind of acid of the etchant in a non-acid mist environment, and calculate concentration of each kind of acid of the etchant according to the absorbance;

wherein the device for measuring concentration of etchant further comprises a one-way pipe configured to communicate the drying tank with the gas tank, the desiccative gas dried by the drying tank returns to the gas tank through the one-way pipe;

wherein the inlet pipe is provided with a first valve for regulating flow rate of the desiccative gas in the gas tank, and the one-way pipe is provided with a second valve for regulating flow rate of the desiccative gas in the drying tank; and the device further comprises a filling tank configured for containing the etchant and connected with the concentration measuring mechanism, the filling tank further configured to supply the etchant to the concentration measuring mechanism in real time;

the acid mist elimination mechanism is configured to eliminate acid mist inside the concentration measuring mechanism by using the desiccative gas in the gas tank to adjust a gas pressure in the concentration measuring mechanism and to bring the acid mist out of the concentration measuring mechanism;

the concentration measuring mechanism comprises a sample cell and a reference cell, the sample cell and the filling tank are bidirectionally connected together, so that the etchant in the filling tank can flow into the sample cell to enable online and real time measurement of the concentration of each kind of acid of the acid mixed etchant, and the measured etchant can flow back into the filling tank through the pipeline to achieve the recycling use of the etchant;

wherein the desiccative gas in the gas tank is air or nitrogen gas; the drying agent is a mixture of calcium oxide and sodium hydroxide; the etchant by weight percentage includes 70%-72% phosphoric acid, 1.8-2.0% nitric acid, 9.5-10.5 acetic acid, and marginal water.

6. A method for measuring concentration of etchant, using a device for measuring concentration of etchant, wherein the device for measuring concentration of etchant comprises a concentration measuring mechanism, a filling tank for supplying etchant to the concentration measuring mechanism, and an acid mist elimination mechanism configured to eliminate acid mist inside the concentration measuring mechanism; the method comprising the following steps:

connecting the acid mist elimination mechanism with the concentration measuring mechanism;

connecting the filling tank with the concentration measuring mechanism;

flowing the etchant in the filling tank into the concentration measuring mechanism, and turning on the acid mist elimination mechanism to extract acid mist from the concentration measuring mechanism, dry the extracted acid mist, and recycle desiccative gas into the concentration measuring mechanism for continuing to extract acid mist;

using the concentration measuring mechanism to measure absorbance of each kind of acid of the etchant in a non-acid mist environment in real time, and calculating concentration of each kind of acid of the etchant according to the absorbance; and the acid mist elimination mechanism comprises a gas tank and a first valve, the first valve is defined in the acid mist elimination mechanism and configured for increasing internal pressure of the concentration measuring mechanism until the internal pressure is equal to or more than external pressure and then to bring the acid mist out of the concentration measuring mechanism; and the dried desiccative gas is recycled into the gas tank;

the device further comprises a filling tank configured for containing the etchant and connected with the concentration measuring mechanism, the filling tank further configured to supply the etchant to the concentration measuring mechanism in real time;

the acid mist elimination mechanism is configured to eliminate acid mist inside the concentration measuring mechanism by using the desiccative gas in the gas tank to adjust a gas pressure in the concentration measuring mechanism and to bring the acid mist out of the concentration measuring mechanism;

the concentration measuring mechanism comprises a sample cell and a reference cell, the sample cell and the filling tank are bidirectionally connected together, so that the etchant in the filling tank can flow into the sample cell to enable online and real time measurement of the concentration of each kind of acid of the acid mixed etchant, and the measured etchant can flow back into the filling tank through the pipeline to achieve the recycling use of the etchant.

* * * * *